United States Patent
Crane et al.

(10) Patent No.: US 9,943,478 B2
(45) Date of Patent: Apr. 17, 2018

(54) COMPOSITIONS CONTAINING FILM FORMING DISPERSION OF PARTICLES IN AQUEOUS PHASE AND HIGH LEVELS OF PLANT OIL

(71) Applicant: L'ORÉAL, Paris (FR)

(72) Inventors: Christine Marie Crane, Watchung, NJ (US); Sandrine Gadol, New York, NY (US); Caroline Francoise Pascale Pujol, Courbevoie (FR); Angeles Fonolla-Moreno, Scotch Plains, NJ (US); Anke Hadasch, Jersey City, NJ (US)

(73) Assignee: L'ORÉAL, Paris (FR)

( * ) Notice: Subject to any disclaimer, the term of this patent is extended or adjusted under 35 U.S.C. 154(b) by 0 days.

(21) Appl. No.: 15/176,527

(22) Filed: Jun. 8, 2016

(65) Prior Publication Data
US 2017/0189322 A1    Jul. 6, 2017

Related U.S. Application Data

(60) Provisional application No. 62/273,345, filed on Dec. 30, 2015.

(51) Int. Cl.
| | |
|---|---|
| A61K 8/97 | (2017.01) |
| A61K 8/92 | (2006.01) |
| A61Q 1/10 | (2006.01) |
| A61K 8/19 | (2006.01) |
| A61K 8/81 | (2006.01) |
| A61K 8/891 | (2006.01) |

(52) U.S. Cl.
CPC ............... *A61K 8/922* (2013.01); *A61K 8/19* (2013.01); *A61K 8/8111* (2013.01); *A61K 8/8147* (2013.01); *A61K 8/891* (2013.01); *A61Q 1/10* (2013.01); *A61K 2800/30* (2013.01); *A61K 2800/43* (2013.01)

(58) Field of Classification Search
CPC .......... A61Q 1/10; A61K 8/922; A61K 47/44
See application file for complete search history.

(56) References Cited

U.S. PATENT DOCUMENTS

| | | | |
|---|---|---|---|
| 3,251,740 A | 5/1966 | Kambersky | |
| 4,795,631 A * | 1/1989 | Sheehan | A61K 8/37 424/64 |
| 7,351,405 B2 * | 4/2008 | De La Poterie | A61K 8/8152 424/70.11 |
| 2004/0170586 A1 | 9/2004 | Ferrari et al. | |
| 2005/0042191 A1 | 2/2005 | Travkina et al. | |
| 2010/0247470 A1 * | 9/2010 | Friel | A61K 8/06 424/70.7 |
| 2015/0079015 A1 | 3/2015 | Bolognini et al. | |
| 2015/0079016 A1 | 3/2015 | Bolognini et al. | |

OTHER PUBLICATIONS

Preedy, V. et al., Nuts & Seeds in Health and Disease Prevention, 2011, pp. 49-50.*

* cited by examiner

*Primary Examiner* — Gina C Justice
(74) *Attorney, Agent, or Firm* — Oblon, McClelland, Maier & Neustadt, L.L.P.

(57) ABSTRACT

The invention relates to a composition, especially a cosmetic composition, comprising at least one dispersion of film forming particles in aqueous phase and high levels of plant oil, as well as to methods of using such compositions.

20 Claims, No Drawings

COMPOSITIONS CONTAINING FILM FORMING DISPERSION OF PARTICLES IN AQUEOUS PHASE AND HIGH LEVELS OF PLANT OIL

CROSS-REFERENCE TO RELATED APPLICATIONS

This application claims the benefit of priority under 35 U.S.C. § 119(e) from U.S. Provisional Application Ser. No. 62/273,345, filed Dec. 30, 2015, the entire contents of which is hereby incorporated by reference.

FIELD OF THE INVENTION

The present invention relates to compositions comprising at least one dispersion of film forming particles in aqueous phase and high levels of plant oils.

DISCUSSION OF THE BACKGROUND

Many cosmetic compositions, including pigmented cosmetics such as foundations, concealers, lipsticks, and mascaras, and other cosmetic and sunscreen compositions, have been formulated in an attempt to impart desired cosmetic properties. For example, mascaras typically contain wax which is used to provide body and volume. However, the tackiness of the wax leads to mascara compositions that clump, apply unevenly, dry the lashes, smudge, flake and are difficult to remove. Also, the tackiness of the wax limits the buildability (layering) and playtime (smoothness) of these waxes. When wax is eliminated from the mascaras to facilitate application and removal, the compositions also lose desirable properties and tend to be runny.

Further, typically the addition of oils to traditional wax-containing mascara formulations (anhydrous or water-containing) can impact negatively the wear of the formula on the lashes, such that the mascara will smudge more.

U.S. Pat. No. 3,251,740 and U.S. patent application publication nos. 2005/0042191, 2015/0079015 and US2015/0079016 disclose mascara products of different composition.

However, there remains a need for improved cosmetic compositions having improved cosmetic properties, particularly mascaras and particularly water-containing mascaras, which are long-wearing, easy to remove, possess good flaking properties and/or possess good smudging properties.

Accordingly, one aspect of the present invention is a water-containing care and/or makeup and/or treatment composition for keratinous material which has good cosmetic properties such as, for example, long-wearing, easy to remove, possess good flaking properties and/or possess good smudging properties.

SUMMARY OF THE INVENTION

The present invention relates to compositions comprising at least one dispersion of film forming particles in aqueous phase and high levels of plant oils. Preferably, the composition is a mascara. Also, preferably, the composition is free of wax. Also, preferably, the composition further comprises at least one non-wax structuring agent.

The present invention also relates to colored compositions comprising at least one coloring agent, at least one dispersion of film forming particles in aqueous phase and high levels of plant oils. Preferably, the composition is a mascara. Also, preferably, the composition is free of wax. Also, preferably, the composition further comprises at least one non-wax structuring agent.

The present invention also relates to methods of treating, caring for and/or making up keratinous material (for example, eyelashes) by applying compositions of the present invention comprising at least one dispersion of film forming particles in aqueous phase and high levels of plant oils, to the keratinous material in an amount sufficient to treat, care for and/or make up the keratinous material. Preferably, the composition is a mascara. Also, preferably, the composition is free of wax. Also, preferably, the composition further comprises at least one non-wax structuring agent.

The present invention also relates to methods of enhancing the appearance of keratinous material (for example, eyelashes) by applying compositions of the present invention comprising at least one dispersion of film forming particles in aqueous phase and high levels of plant oils, to the keratinous material in an amount sufficient to enhance the appearance of the keratinous material. Preferably, the composition is a mascara. Also, preferably, the composition is free of wax. Also, preferably, the composition further comprises at least one non-wax structuring agent.

The present invention also relates to methods of reducing stiffness of a film formed by at least one dispersion of film forming particles in aqueous phase comprising combining high levels of plant oils with the at least one dispersion of film forming particles in an amount sufficient to reduce the stiffness of the film. Preferably, the at least one dispersion of film forming particles in aqueous phase and high levels of plant oils are combined in a composition which is a mascara. Also, preferably, the composition is free of wax. Also, preferably, the composition further comprises at least one non-wax structuring agent.

The present invention further relates to kits containing a composition of the present invention comprising at least one dispersion of film forming particles in aqueous phase and high levels of plant oils, and a topcoat composition. Preferably, the composition is a mascara. Also, preferably, the composition is free of wax. Also, preferably, the composition further comprises at least one non-wax structuring agent.

It is to be understood that both the foregoing general description and the following detailed description are exemplary and explanatory only, and are not restrictive of the invention.

DETAILED DESCRIPTION OF THE INVENTION

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.8%-2.2%).

"A" or "an" as used herein means "at least one."

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Film former", "film-forming polymer" or "film forming agent" or "co-film former" as used herein means a polymer or resin that leaves a film on the substrate to which it is applied, for example, after a solvent accompanying the film former has evaporated, absorbed into and/or dissipated on the substrate.

"Wax" as used herein is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state.

"Free" or "devoid" of as it is used herein means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "free of solvents" means that non-aqueous solvents are preferably omitted (that is 0% by weight), but can be present in the composition at an amount of less than about 0.1% by weight, typically less than about 0.05% by weight, based on the total weight of the composition.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to keratin materials such as eyelashes and evaluating the color of the composition after an extended period of time. For example, the color of a composition may be evaluated immediately following application to keratin materials such as eyelashes and these characteristics may then be re-evaluated and compared after a certain amount of time. Further, these characteristics may be evaluated with respect to other compositions, such as commercially available compositions.

"Making up" as used herein means to provide decoration (for example, color) to keratin materials such as the eyelashes.

"Protecting" as used herein means to inhibit damage to keratin materials such as the eyelashes by providing a protective layer on the keratin materials.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Young's modulus" as used herein, means a force per unit area (MPa) that is needed to stretch a sample material. It is defined as the slope of stress-strain curve at the elastic region where the deformation of the sample can be restored to its original state. Stress is the force causing deformation divided by the area to which the force is applied and the strain is the deformation ratio in length to its original state. The high value of Young's modulus means that the material is hard and stiff, on the contrary low value means that the material is soft, flexible and more ductile.

"Water resistance" as used herein, means resistance of a material (substance) to the penetration of water, which may cause degradation of that material. The method implemented if assessment of this invention is further disclosed.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

The compositions and methods of the present invention can comprise, consist of, or consist essentially of the essential elements and limitations of the invention described herein, as well as any additional or optional ingredients, components, or limitations described herein or otherwise useful.

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

Dispersion of Film Forming Particles

According to the present invention, compositions comprising at least one dispersion of film forming particles in aqueous phase are provided. The dispersion of film forming particles in aqueous phase is more generally known as latex.

Suitable polymers for the film-forming particles that may be used in the compositions of the present invention include, but are not limited to, synthetic polymers, free-radical type or polycondensate type polymers, polymers of natural origin, and mixtures thereof.

Preferably, the polymers for the film-forming particles may be selected from vinyl (co)polymers, (meth)acrylic (co)polymers, urethanes (co)polymers, and mixtures thereof. Advantageously, the polymer for the film-forming particles is selected from a styrene-(meth)acrylic and (meth) acrylic copolymer, a vinyl acetate and (meth)acrylic copolymer, and mixtures thereof.

Polymers for the film-forming particles of the free-radical type may be chosen, for example, from vinyl polymers or copolymers, such as acrylic polymers.

Vinyl film-forming polymers can result from the polymerization of monomers comprising at least one ethylenic unsaturation and at least one acidic group and/or esters of these acidic monomers and/or amides of these acidic monomers. Monomers comprising at least one acid group which may be used include, for example, $\alpha,\beta$-ethylenic unsaturated carboxylic acids such as acrylic acid, methacrylic acid, crotonic acid, maleic acid or itaconic acid. (Meth)acrylic acid and crotonic acid are, for example, used. Preferably, (meth)acrylic acid is used.

The esters of acidic monomers can be chosen, for example, from (meth)acrylic acid esters (also known as (meth)acrylates), such as (meth)acrylates of an alkyl, for example, a C1-C30 alkyl, such as a C1-C20 alkyl, (meth) acrylates of an aryl, such as a C6-C10 aryl, and (meth) acrylates of a hydroxyalkyl, such as a C2-C6 hydroxyalkyl. Among the alkyl (meth)acrylates that may be mentioned, examples include methyl methacrylate, ethyl methacrylate, butyl methacrylate, isobutyl methacrylate, 2-ethylhexyl methacrylate, lauryl methacrylate and cyclohexyl methacrylate. Among the hydroxyalkyl (meth)acrylates that may be mentioned, examples include hydroxyethyl acrylate, 2-hydroxypropyl acrylate, hydroxyethyl methacrylate and 2-hydroxypropyl methacrylate. Among the aryl (meth)acrylates that may be mentioned, examples include benzyl acrylate and phenyl acrylate. The (meth)acrylic acid esters that may be used are, for example, alkyl (meth)acrylates.

The alkyl group of the esters may be substituted. For example, the alkyl group of the esters may be either fluorinated or perfluorinated, i.e., some or all of the hydrogen atoms of the alkyl group are substituted with fluorine atoms. Further, examples of amides of the acid monomers that may be mentioned include (meth)acrylamides, such as N-alkyl (meth)acrylamides, for example, of a $C_2$-$C_{12}$ alkyl. Among the N-alkyl(meth)acrylamides that may be mentioned, examples include N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. For example, these monomers may be polymerized with acid monomers and/or esters thereof and/or amides thereof, such as those mentioned above. Examples of vinyl esters that may be mentioned include vinyl acetate, vinyl neodecanoate, vinyl pivalate, vinyl benzoate and vinyl t-butylbenzoate. Styrene monomers that may be mentioned include styrene and $\alpha$-methylstyrene.

Among the film-forming polycondensates that may be mentioned, examples include polyurethanes, polyesters, polyesteramides, polyamides, epoxyester resins and polyureas.

The polyurethanes may be chosen from anionic, cationic, nonionic or amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

The polyesters may be obtained, in a known manner, by polycondensation of dicarboxylic acids with polyols, such as diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalene-dicarboxylic acid and 2,6-naphthalenedicarboxylic acid. These dicarboxylic acid monomers may be used alone or as a combination of at least two dicarboxylic acid monomers. Among these monomers, phthalic acid, isophthalic acid and terephthalic acid may, for example, be used.

The diol may be chosen from aliphatic, alicyclic and aromatic diols. The diol used is, for example, chosen from ethylene glycol, diethylene glycol, triethylene glycol, 1,3-propanediol, cyclohexanedimethanol and 4-butanediol. Other polyols that may be used include glycerol, pentaerythritol, sorbitol and trimethylolpropane.

The polyesteramides may be obtained in a manner analogous to that of the polyesters, by polycondensation of diacids with diamines or amino alcohols. Diamines that may be used include, for example, ethylenediamine, hexamethylenediamine and meta- or para-phenylenediamine. An amino alcohol that may be used is, for example, monoethanolamine.

The polyester may also comprise at least one monomer bearing at least one —$SO_3M$ group, wherein M is chosen from a hydrogen atom, an ammonium ion $NH_4^+$ and a metal ion such as an $Na^+$, $K^+$, $Mg^{2+}$, $Ca^{2+}$, $Cu^{2+}$, $Fe^{2+}$ or $Fe^{3+}$ ion. A difunctional aromatic monomer comprising such an —$SO_3M$ group may, for example, be used.

The aromatic nucleus of the difunctional aromatic monomer also comprising an —$SO_3M$ group as described above may be chosen, for example, from benzene, naphthalene, anthracene, biphenyl, oxybiphenyl, sulfonylbiphenyl and methylenebiphenyl nuclei. Among the difunctional aromatic monomers also comprising an —$SO_3M$ group, mention may be made, for example, of sulfoisophthalic acid, sulfoterephthalic acid, sulfophthalic acid, 4-sulfonaphthalene-2, 7-dicarboxylic acid.

The copolymers used are, for example, those based on isophthalate/sulfoisophthalate, such as copolymers obtained by condensation of diethylene glycol, cyclohexanedimethanol, isophthalic acid and sulfoisophthalic acid.

The polymer for the film forming particles may also be a liposoluble polymer. Examples of the liposoluble polymer that may be mentioned include copolymers of a vinyl ester (wherein the vinyl group is directly linked to the oxygen atom of the ester group and the vinyl ester comprises a radical chosen from saturated, linear or branched hydrocarbon-based radicals of 1 to 19 carbon atoms, linked to the carbonyl of the ester group) and of at least one other monomer, which may be a vinyl ester (different from the vinyl ester already present), an $\alpha$-olefin (comprising from 8 to 28 carbon atoms), an alkyl vinyl ether (the alkyl group of which comprises from 2 to 18 carbon atoms) or an allylic or methallylic ester (comprising a radical chosen from saturated, linear or branched hydrocarbon-based radicals of 1 to 19 carbon atoms, linked to the carbonyl of the ester group).

These copolymers may be crosslinked using crosslinking agents that may be either of the vinylic type or of the allylic or methallylic type, such as tetraallyloxyethane, divinylbenzene, divinyl octanedioate, divinyl dodecanedioate and divinyl octadecanedioate.

Examples of these copolymers which may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Further examples of the liposoluble film-forming polymers include liposoluble copolymers, such as those resulting from the copolymerization of vinyl esters comprising from 9 to 22 carbon atoms or of alkyl acrylates or methacrylates, wherein the alkyl radicals comprise from 10 to 20 carbon atoms. Such liposoluble copolymers may be chosen, for example, from polyvinyl stearate, polyvinyl stearate crosslinked with the aid of divinylbenzene, of diallyl ether or of diallyl phthalate copolymers, polystearyl (meth)acrylate, polyvinyl laurate and polylauryl (meth)acrylate copolymers, it being possible for these poly(meth)acrylates to be crosslinked with the aid of ethylene glycol dimethacrylate or tetraethylene glycol dimethacrylate. The liposoluble copolymers described above are known and are described, for example, in French patent application FR-A-2 232 303; they may have a weight-average molecular weight ranging, for example, from 2,000 to 500,000 such as from 4,000 to 200,000.

Among the liposoluble film-forming polymers which may be used herein, mention may also be made, for example, of polyalkylenes such as copolymers of $C_2$-$C_{20}$ alkenes, such as polybutene, alkylcelluloses with a linear or branched, saturated or unsaturated $C_2$-$C_8$ alkyl radical, for instance ethylcellulose and propylcellulose, copolymers of vinylpyrrolidone (VP) such as copolymers of vinylpyrrolidone and of $C_2$-$C_{40}$ alkene such as $C_3$-$C_{20}$ alkene. Among the VP copolymers which may be used herein, mention may be made, for example, of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

Specific examples of aqueous dispersions of film-forming particles which may be used are the acrylic dispersions sold under the names "Neocryl XK-90®", "Neocryl A-1070®", "Neocryl A-1090®", "Neocryl BT-62®", "Neocryl A-1079®" and "Neocryl A-523®" by the company Avecia-Neoresins, "Dow Latex 4320" by the company Dow Chemical, "Daitosol 5000 AD®" or "Daitosol 5000 SJ" by the company Daito Kasey Kogyo; the aqueous dispersions of polyurethane sold under the names "Neorez R-981®" and "Neorez R-974®" by the company Avecia-Neoresins, "Avalure UR-405®", "Avalure UR-410®", "Avalure UR-425®", "Avalure UR-450®", "Sancure 875®", "Sancure 861®", "Sancure 878®" and "Sancure 206®" by the company Goodrich, "Impranil 85®" by the company Bayer and "Aquamere H-151®" by the company Hydromer; vinyl dispersions, for instance "Mexomer PAM" and also acrylic dispersions in isododecane, for instance "Mexomer PAP" by the company Chimex.

Further specific examples of latex polymers for use in the present invention further include ethylhexyl acrylate/hema copolymer (and) acrylates/diethylaminoethyl methacrylate/ethylhexyl acrylate copolymer (Syntran®PC 5775), styrene/acrylates/ammonium methacrylate copolymer (Syntran®5760, Syntran®5009, Syntran®PC5620), polyacrylate-21 (and) acrylates/dimethylaminoethyl methacrylate copolymer (Syntran®PC5100, Syntran®PC5776, Eudragit®E 100, Jurymer ET-410C), styrene/acrylates/ammonium methacrylate copolymer (Syntran®5009 CG), olefin/acrylate grafted polymer (and) sodium laureth sulfate (and C12-15 SEC-pareth 15 (Syntran®EX108), acrylates copolymer (Aculyn®33A Polymer, Avalure®Ace 210/120/315 Acrylic Copolymer, Carbopol® Aqua SF-1 Polymer, Coatex®Co 633, Eliclear®380/700/4U, Eudragit® L 100, Joncryl®85, Luviflex®Soft), acrylates/ethylhexyl acrylate copolymer. The Syntran® polymers are commercially available from the supplier Interpolymer Corp.

Preferably, the film forming particles are present in the compositions of the present invention in an amount sufficient to form a film upon a substrate to which it has been applied (for example, eyelashes). When the film forming particles are in the form of a commercial product containing the film forming particles in aqueous dispersion, the amount of active material (that is, film forming particles) within the aqueous dispersion is sufficient to form a film upon a substrate to which it has been applied. Preferably, the film forming particles are present in the compositions of the present invention in amounts of active material generally ranging from about 1% % to about 50%, preferably from about 1% to about 30%, preferably from about 2% to about 20%, and more preferably from about 5% to about 15%, by weight, based on the total weight of the composition, including all ranges and subranges in between.

High Levels of Plant Oil

According to the present invention, compositions comprising high levels of plant oil are provided. As used herein, "plant oil" means hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil, musk rose oil, argan oil, camellia oil, linseed oil, China wood oil, oiticica oil, coconut oil, olive oil, palm oil, peanut oil, and tall oil.

According to the present invention, compositions comprising at least one polar plant oil are provided. As used herein, "polar plant oil" means a plant oil containing at least one fatty acid ester of glycerol having at least one hydroxyl group (OH). A suitable example of a polar plant oil is castor oil.

Preferably, the polar plant oil is present in the compositions of the present invention in amounts of active material generally ranging from about 0.1% to about 20%, preferably from about 0.5% to about 10%, preferably from about 0.6% to about 7.5%, and preferably from about 1.0% to about 5%, by weight, based on the total weight of the composition, including all ranges and subranges in between.

According to preferred embodiments of the present invention, the compositions of the present invention further comprise at least one non-polar plant oil. As used herein, "non-polar plant oil" means a plant oil containing at least one fatty acid ester of glycerol that does not have at least one hydroxyl group (OH). A suitable example of a non-polar plant oil is camellia oil or argan oil.

Preferably, the non-polar plant oil is present in the compositions of the present invention in amounts of active material generally ranging from about 0.075% to about 15%, preferably from about 0.1% to about 7.5%, preferably from about 0.2% to about 6%, and preferably from about 0.3% to about 5%, by weight, based on the total weight of the composition, including all ranges and subranges in between.

Although not wishing to be bound by any particular theory, it is believed that adding high levels of polar plant oil such as castor oil enables more total oil to be added to the compositions of the present invention without adversely affecting the cosmetic properties of the compositions because of presence of a C12 hydroxyl group in castor oil. Accordingly, generally speaking, it is believed that the more polar plant oil that is present, the more total oil including non-polar plant oil that can be added to the compositions of the present invention.

Preferably, more polar plant oil is present in the compositions of the present invention than non-polar plant oil.

Preferably, polar plant oil and non-polar plant oil are present in the compositions of the present invention in a polar plant oil to non-polar plant oil weight ratio of from 7:1 to 1:7, preferably from 4:1 to 1:4, preferably from 4:1 to 1:1, preferably from 3:1 to 1:1, preferably from 2.5:1 to 1:1, including all ranges and subranges therebetween.

Preferably, film forming particles (active material) and polar plant oil are present in the compositions of the present invention in a film forming particles to polar plant oil weight ratio of from 50:1 to 1:50, preferably from 40:1 to 1:40, preferably from 40:1 to 1:4, preferably from 10:1 to 1:1, preferably from 8:1 to 1:1, and preferably from 5:1 to 1:1, including all ranges and subranges therebetween.

Preferably, film forming particles (active material) and total plant oil are present in the compositions of the present invention in a film forming particles to total plant oil weight ratio of from 30:1 to 1:30, preferably from 20:1 to 1:20, preferably from 20:1 to 1:5, preferably from 10:1 to 1:4, preferably from 5:1 to 1:3, and preferably from 4:1 to 1:3, including all ranges and subranges therebetween.

Non-Wax Structuring Agent

According to preferred embodiments of the present invention, the compositions of the present invention may optionally further comprise at least one non-wax structuring agent.

Preferably, the non-wax structuring agent is a naturally-derived substance which has the ability to create a gel structure and/or thicken the composition. Preferably, the non-wax structuring agent is suitable for use as a substitute for montan-wax. Preferably, the non-wax structuring agent is a copolymer comprising at least one sugar or sugar alcohol such as, for example, sorbitol or mannitol; at least one fatty dicarboxylic acid, wherein the fatty portion contains at least 8 carbon atoms; and at least one fatty acid (as defined above).

Suitable examples of such structuring agents include, but are not limited to, Syncrowax™ OSW and Syncrowax™ ORM available from Croda. Syncrowax™ ORM has the INCI name sorbitol/sebacic acid copolymer behenate. Syncrowax™ OSW is a blend of Tribehenin and Syncrowax™ ORM.

Preferably, the non-wax structuring agent is present in the compositions of the present invention in amounts of active material generally ranging from about 0.075% to about 15%, preferably from about 0.1% to about 7.5%, preferably from about 0.2% to about 5%, and preferably from about 0.5% to about 2.5%, by weight, based on the total weight of the composition, including all ranges and subranges in between.

Oil Phase

According to embodiments of the present invention, the compositions of the present invention may optionally further comprise at least one non-plant oil. "Oil" means any non-aqueous medium which is liquid at ambient temperature (25° C.) and atmospheric pressure (760 mm Hg).

Suitable non-plant oils include volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Suitable non-plant oils include non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Suitable non-plant oils include synthetic oils or esters of formula $R_6COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7\geq10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; pentaerythritol esters; and synthetic ethers containing from 10 to 40 carbon atoms.

If present, the at least one non-plant oil is present in the compositions of the present invention in an amount ranging from about 0.1% to about 7.5% by weight, more preferably from about 0.1% to about 5% by weight, and preferably from about 0.1% to about 4.5% by weight, based on the total weight of the composition, including all ranges and subranges within these ranges.

However, according to particularly preferred embodiments of the present invention, the compositions of the present invention are free of non-plant oils.

According to preferred embodiments of the present invention, the compositions of the present invention may further comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C., silicone waxes, such as alkyl- or alkoxydimethicones having an alkyl or alkoxy chain ranging from 10 to 45 carbon atoms, poly(di) methylsiloxane esters which are solid at 30° C. and whose ester chain comprising at least 10 carbon atoms, or else di(1,1,1-trimethylolpropane) tetrastearate, which is sold or manufactured by Heterene under the name HEST 2T-4S, and mixtures thereof.

If present, the wax or waxes may be present in an amount ranging from about 0.1% to about 5% by weight, more preferably from about 0.1% to about 3% by weight, and preferably from about 0.1% to about 1% by weight, based on the total weight of the composition, including all ranges and subranges within these ranges. However, according to particularly preferred embodiments of the present invention, the compositions of the present invention are wax-free.

Coloring Agents

According to preferred embodiments of the present invention, compositions optionally further comprising at least one coloring agent are provided. Preferably, such colored compositions can be cosmetic compositions such as mascaras.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Additional Additives

The composition of the invention can also comprise any additive usually used in the field under consideration. For example, dispersants such as poly(12-hydroxystearic acid), antioxidants, film forming agents, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* (9th ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

According to preferred embodiments of the present invention, methods of treating, caring for and/or making up keratinous material such as skin, lips, eyes and eyelashes by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

In accordance with the preceding preferred embodiments, the compositions of the present invention are applied topically to the desired area of the keratin material in an amount sufficient to treat, care for and/or make up the keratinous material, or to enhance the appearance of keratinous material. The compositions may be applied to the desired area as needed, preferably once or twice daily, more preferably once daily and then preferably allowed to dry before subjecting to contact such as with clothing or other objects (for example, a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to other embodiments of the present invention, methods of methods of reducing stiffness of a film formed by at least one dispersion of film forming particles in aqueous phase are provided. These methods comprise combining high levels of plant oil with the at least one dispersion of film forming particles in aqueous phase in an amount sufficient to reduce the stiffness of a film formed by the at least one dispersion of film forming particles in aqueous phase. Preferably, the at least one dispersion of film forming particles in aqueous phase and high levels of plant oil are combined in a composition which is a mascara. Also, preferably, the composition is free of wax. Also, preferably, the composition further comprises at least one non-wax structuring agent.

According to such methods, preferably, the high levels of plant oil are combined in an amount sufficient to reduce stiffness of the film formed by the film forming particles upon application to a substrate (for example, eyelashes). For example, preferably, the plant oils are present in an amount sufficient to reduce the Young's modulus of the composition.

According to such methods, preferably, the polar plant oil is present in the compositions of the present invention in amounts of active material generally ranging from about 0.1% to about 20%, preferably from about 0.5% to about 10%, preferably from about 0.6% to about 7.5%, and preferably from about 1% to about 5%, by weight, based on the total weight of the composition, including all ranges and subranges in between.

According to such methods, preferably, the non-polar plant oil is present in the compositions of the present invention in amounts of active material generally ranging from about 0.075% to about 15%, preferably from about 0.1% to about 7.5%, preferably from about 0.2% to about 6%, and preferably from about 0.3% to about 5%, by weight, based on the total weight of the composition, including all ranges and subranges in between.

According to such methods, preferably, more polar plant oil is present in the compositions of the present invention than non-polar plant oil.

According to such methods, preferably, polar plant oil and non-polar plant oil are present in the compositions of the present invention in a polar plant oil to non-polar plant oil weight ratio of from 7:1 to 1:7, preferably from 4:1 to 1:4, preferably from 4:1 to 1:1, preferably from 3:1 to 1:1, preferably from 2.5:1 to 1:1, including all ranges and subranges therebetween.

According to such methods, preferably, film forming particles (active material) and polar plant oil are present in the compositions of the present invention in a film forming particles to polar plant oil weight ratio of from 50:1 to 1:50, preferably from 40:1 to 1:40, preferably from 40:1 to 1:4, preferably from 10:1 to 1:1, preferably from 8:1 to 1:1, and preferably from 6:1 to 1:1, including all ranges and subranges therebetween.

According to such methods, preferably, film forming particles (active material) and total plant oil are present in the compositions of the present invention in a film forming particles to total plant oil weight ratio of from 30:1 to 1:30, preferably from 20:1 to 1:20, preferably from 20:1 to 1:5, preferably from 10:1 to 1:4, preferably from 5:1 to 1:3, and preferably from 4:1 to 1:3, including all ranges and subranges therebetween.

Unless otherwise indicated, all numbers expressing quantities of ingredients, reaction conditions, and so forth used in the specification and claims are to be understood as being modified in all instances by the term "about," Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example I

Sample Formulation

|  | INCI Name/Supplier | % |
|---|---|---|
| Dispersion of Film Forming Particles in Aqueous Phase | Syntran 5760, Interpolymer | 2%-20% (active polymer) |
| Oil-Soluble Film Former | Indopol H 1500, Ineos | 0.5-5% |
| Structuring Agent | Syncrowax ORM PW-MV, Croda | 0.2-5% |
| Polar Oil |  | 0.5-7.5% |
| Non-Polar Oil |  | 0.1-3% |
|  |  | 0.1-3% |
| Pigments | Sunpuro Iron Oxides, SUN Chemical | 3-20% |

Example II

Formulations Preparation

The following compositions in Examples III-VI were prepared in the following manner:

Water was heated to 60-70° C. with agitation using a large chopping blade (100 rpm).

Water was charged with pigments, preservatives, water-soluble thickeners, water-soluble emulsifiers, and plasticizers and mixed with a large rotor-stator homogenizer at 500-900 rpm until pigments dispersed (approx. 1 hr).

Oils, liquid fats, oil-soluble emulsifiers and film formers were melted at 70-90° C. and added to water phase using large rotor-stator homogenizer at 900-1200 rpm and emulsified for 30 minutes at 70-80° C.

Once emulsified the composition was cooled to 50-60° C.

Temperature sensitive latex and silicone film former dispersions were then added and mixed for 20 minutes (1200 rpm).

The homogenizer was switched to slow sweeper blade and cooled to <30° C.

Example III

Actual Formulations

Reference Example 1 and Invention Examples 1 through 11 were prepared:

|  | INCI | Ref. 1 | Ex. 1 | Ex. 6 | Ex. 9 | Ex. 2 | Ex. 5 | Ex. 8 |
|---|---|---|---|---|---|---|---|---|
| SOLVENT | WATER | 45.169 | 46.1690 | 48.669 | 50.169 | 46.1690 | 48.669 | 50.169 |
| PIGMENT | IRON OXIDES | 10 | 10 | 10 | 10 | 10 | 10 | 10 |
| FILM FORMER | STYRENE/ ACRYLATES/ AMMONIUM METHACRYLATE COPOLYMER POLYBUTENE DIVINYLDIMETHICONE/ DIMETHICONE COPOLYMER | 12.068 | 12.068 | 12.068 | 12.068 | 12.068 | 12.068 | 12.068 |
| EMULSIFIER/ SURFACTANT | PEG-200 GLYCERYL STEARATE GLYCERYL STEARATE BEHENYL ALCOHOL GLYCERYL STEARATE CITRATE DISODIUM ETHYLENE DICOCAMIDE PEG-15 DISULFATE PEG-100 STEARATE SODIUM LAURETH SULFATE C12-13 PARETH-23 C12-13 PARETH-3 | 12.464 | 12.464 | 12.464 | 12.464 | 12.464 | 12.464 | 12.464 |
| OIL | NON-POLAR OIL (a) |  | 5 | 2.5 | 1 |  |  |  |
|  | NON-POLAR OIL (b) |  |  |  |  | 5 | 2.5 | 1 |
| LIQUID FATTY SUBSTANCE | DIMETHICONE DIMETHICONOL DIMETHICONE/ VINYL DIMETHICONE CROSSPOLYMER | 4 | 4 | 4 | 4 | 4 | 4 | 4 |
| OIL PHASE GELLANT | SORBITOL/SEBACIC ACID COPOLYMER BEHENATE TRIBEHENIN GLYCERYL DIBEHENATE GLYCERYL BEHENATE | 2.5 | 2.5 | 2.5 | 2.5 | 2.5 | 2.5 | 2.5 |
| PRESERVATIVE | PHENOXYETHANOL CAPRYLYL GLYCOL POTASSIUM SORBATE DISODIUM EDTA TETRASODIUM EDTA | 1.559 | 1.559 | 1.559 | 1.559 | 1.559 | 1.559 | 1.559 |
| HUMECTANT | GLYCERIN BUTYLENE GLYCOL PROPYLENE GLYCOL | 5.24 | 5.24 | 5.24 | 5.24 | 5.24 | 5.24 | 5.24 |
| GELLANT | AMMONIUM POLYACRYLOYL- DIMETHYL TAURATE XANTHAN GUM | 0.8 | 0.8 | 0.8 | 0.8 | 0.8 | 0.8 | 0.8 |
| ANTIOXIDANT |  | 0.2000 | 0.2000 | 0.2000 | 0.2000 | 0.2000 | 0.2000 | 0.2000 |
| FILLER |  | 6 |  |  |  |  |  |  |

|  | INCI | Ex. 3 | Ex. 4 | Ex. 7 | Ex. 11 | Ex. 10 |
|---|---|---|---|---|---|---|
| SOLVENT | WATER | 46.1690 | 48.669 | 50.169 | 46.1690 | 47.6690 |
| PIGMENT | IRON OXIDES | 10 | 10 | 10 | 10 | 10 |
| FILM FORMER | STYRENE/ ACRYLATES/ AMMONIUM METHACRYLATE COPOLYMER POLYBUTENE | 12.068 | 12.068 | 12.068 | 12.068 | 12.068 |

-continued

| | INCI | Ex. 3 | Ex. 4 | Ex. 7 | Ex. 11 | Ex. 10 |
|---|---|---|---|---|---|---|
| EMULSIFIER/ SURFACTANT | DIVINYLDIMETHICONE/ DIMETHICONE COPOLYMER PEG-200 GLYCERYL STEARATE GLYCERYL STEARATE BEHENYL ALCOHOL GLYCERYL STEARATE CITRATE DISODIUM ETHYLENE DICOCAMIDE PEG-15 DISULFATE PEG-100 STEARATE SODIUM LAURETH SULFATE C12-13 PARETH-23 C12-13 PARETH-3 | 12.464 | 12.464 | 12.464 | 12.464 | 12.464 |
| OIL | POLAR (and) NON-POLAR OIL | 5 | 2.5 | 1 | 5 | 3.5 |
| LIQUID FATTY SUBSTANCE | DIMETHICONE DIMETHICONOL DIMETHICONE/ VINYL DIMETHICONE CROSSPOLYMER | 4 | 4 | 4 | 4 | 4 |
| OIL PHASE GELLANT | SORBITOL/SEBACIC ACID COPOLYMER BEHENATE TRIBEHENIN GLYCERYL DIBEHENATE GLYCERYL BEHENATE | 2.5 | 2.5 | 2.5 | 2.5 | 2.5 |
| PRESERVATIVE | PHENOXYETHANOL CAPRYLYL GLYCOL POTASSIUM SORBATE DISODIUM EDTA TETRASODIUM EDTA | 1.559 | 1.559 | 1.559 | 1.559 | 1.559 |
| HUMECTANT | GLYCERIN BUTYLENE GLYCOL PROPYLENE GLYCOL | 5.24 | 5.24 | 5.24 | 5.24 | 5.24 |
| GELLANT | AMMONIUM POLYACRYLOYL-DIMETHYL TAURATE XANTHAN GUM | 0.8 | 0.8 | 0.8 | 0.8 | 0.8 |
| ANTIOXIDANT FILLER | | 0.2000 | 0.2000 | 0.2000 | 0.2000 | 0.2000 |

Example IV

Commercial Products

Commercial Product A: AQUA/WATER/EAU, PARAFFIN, GLYCERYL STEARATE, COPERNICIA CERIFERA CERA/COPERNICIA CERIFERA (CARNAUBA) WAX/CIRE DE CARNAUBA, PVP, CERA ALBA/BEESWAX/LIRE D'ABEILLE, PROPYLENE GLYCOL, TRIBEHENIN, POLYSORBATE 20, STEARIC ACID, AMMONIUM ACRYLATES COPOLYMER, PANTHENOL, CAPRYLYL GLYCOL, HYDROXYETHYLCELLULOSE, TOCOPHERYL ACETATE, ARGANIA SPINOSA KERNEL OIL, SODIUM HYDROXIDE, TALC, ACRYLATES/CARBAMATE COPOLYMER, ASCORBYL GLUCOSIDE, GOSSYPIUM HERBACEUM (COTTON) POWDER, SERICA POWDER/SILK POWDER/POUDRE DE SOIE, RETINYL PALMITATE, HYDROGENATED VEGETABLE OIL, GLYCERIN, COLLAGEN, HYDROGENATED OLIVE OIL, OLEA EUROPAEA (OLIVE) FRUIT OIL, HYDROLYZED KERATIN, PRUNUS ARMENIACA (APRICOT) KERNEL OIL, SODIUM SULFATE, CERAMIDE 2, OLEA EUROPAEA (OLIVE) OIL UNSAPONIFIABLES, POTASSIUM SORBATE, PHENOXYETHANOL, BAMBUSA ARUNDINACEA LEAF EXTRACT, SODIUM BENZOATE, TOCOPHEROL.

[May Contain/Peut Contenir/+/−: IRON OXIDES (CI 77491, CI 77492, CI 77499, CI 77491), TITANIUM DIOXIDE (CI 77891), FERRICFERROCYANIDE (CI 77510), CARMINE (CI 75470), CHROMIUM HYDROXIDE GREEN (CI 77289), CHROMIUM OXIDE GREENS (CI 77288), IRON OXIDES (CI 77491, CI 77492, CI 77499) (CI 77491, CI 77492, CI 77499), ULTRAMARINES (CI 77007), MICA]

Commercial Product B: Water, Beeswax, Sucrose Stearate, Propanediol, Cetearyl Alcohol, Rice Bran Wax, C18-36 Acid Triglyceride, Acrylates/Ethylhexyl Acrylate Copolymer, VP/Eicosene Copolymer, Phenoxyethanol, Hydroxyethylcellulose, *Myrica Pubescens* Fruit Cera (*Myrica Pubescens* Fruit Wax), Silica, Panthenol, Organic Argan Kernel Oil, Ethylhexylglycerin, Laureth-21, Glycerin, *Bambusa Vulgaris* Leaf/Stem Extract, Potassium Sorbate. May Contain: Iron Oxides (CI 77499).

Commercial Product C: Water, Paraffin, Cyclomethicone, Stearic Acid, Beeswax, Triethanolamine, Acacia, Carnauba Wax, Dimethiconol, 2-Oleamido-1, 3-Octadecanediol, Hydroxyethylcellulose, Sodium Polymethacrylate, Panthenol, Imidazolidinyl Urea, Methylparaben, Ethoxydiglycol, Propylparaben, Simethicone, Polyquaternium-10. May Contain: Iron Oxides, Titanium Dioxide, Ultramarines.

Commercial Product D: WATER/AQUA, STYRENE/ACRYLATES/AMMONIUM METHACRYLATE COPOLYMER, BEESWAX/CERA ALBA, IRON OXIDES/CI 77499, SIMMONDSIA CHINENSIS (JOJOBA) BUTTER/SIMMONDSIA CHINENSIS BUTTER, STEARETH-20, ACACIA, SENEGAL GUM, ALCOHOL DENAT, POTASSIUM CETYL PHOSPHATE, STEARETH-2, COPERNICIA CERIFERA (CARNAUBA) WAX/COPERNICIA CERIFERA CERA, VP/EICOSENE COPOLYMER, BUTYLENE GLYCOL, HYDROXYETHYLCELLULOSE, PHENOXYETHANOL, CAPRYLYL GLYCOL, SODIUM DEHYDROACETATE, SODIUM LAURETH-12 SULFATE, PEG/PPG-17/18 DIMETHICONE, DISODIUM EDTA, POTASSIUM SORBATE, METHYLPARABEN, TETRASODIUM EDTA, PROPYLPARABEN, SOLUBLE COLLAGEN Commercial Product E: Water, Paraffin, Potassium Cetyl Phosphate, Beeswax, Carnauba Wax, Acacia Senegal Gum, Glycerin, Cetyl Alcohol, Hydroxyethylcellulose, Sodium Polymethacrylate, Hydrogenated Jojoba Oil, Hydrogenated Palm Oil, Phenethyl Alcohol, Phenoxyethanol, Steareth 20, PEG/PPG 17/18 Dimethicone, Polyquaternium 10, Silica, Soluble Collagen, Simethicone, Panthenol, Disodium EDTA, May Contain (+/−): Iron Oxides (CI 77491, CI 77492, CI 77499), Titanium Dioxide (CI 77891), Ultra marines (CI 77007), Chromium Oxide Greens (CI 77288), Chromium Hydroxide Green (CI 77289), Manganese Violet (CI 77742), Ferric Ferrocyanide (CI 77510), Mica.

Example V

Testing Protocols

Viscosity Determination: The viscosity of the formulas were measured at 25° C. with a Brookfield DV2T viscometer in the absence of the guard leg, at 20 rmp (revolutions per minute) using a No. 7 spindle (hereinafter, "Method A"). The reported viscosity was that measured 10 minutes after switching on the rotation of the spindle (when a constant torque is read) and the values are reported in Pa*s.

pH Determination: pH was determined using a Denver Scientific Ultrabasic pH Meter with a 3 mol/L KCl probe.

Texture Analysis: Experiments were performed on a TA.XT Plus Texture Analyzer with a cylindrical TA-Delrin probe (10 mm diameter) in 6×2 cm stainless steel cups, filled with bulk at 25° C. Surface was cut with stainless steel blade to ensure flat top surface. Settings: Test Mode: compression, Pre-test speed: 2 mm/sec, post-test speed: 2 mm/sec, test speed: 0.5 mm/sec, target mode: distance, distance: 5 mm, trigger force: auto, trigger force: 2 grams. After penetrating the sample, the probe returned to its initial position. The curve generated was a plot of force (grams) as a function of time (seconds). When a 2 g surface trigger was attained, the probe proceeded to penetrate to a depth of 5 mm. At this point (maximum+ve force), the probe returned to its original position at constant speed (e.g. 2.0 mm/s). The maximum+ve force (hardness, grams) gave an indication of the softness of the sample. The smaller the peak force value the softer was the sample. Data repeated in triplicate and reported ±standard deviation.

Extreme Flake: Experiments were run in triplicate. 30 strokes of product were applied to fake eyelashes in 15 stroke sets with a 30 second pause between second application. Samples were allowed to dry 16-24 hours. Sample was held in place in a polystyrene weigh boat and brushed 10 times with a dry bristle mascara brush. Flakes were collected with tape and rated comparatively. A ranking of 1 was better than reference and rating of 2 was equal to reference and a rating of 3 was worse than reference, where the reference was Reference Example 1.

Extreme Smudge: Experiments were run in triplicate. 30 strokes of product were applied to fake eyelashes in 15 stroke sets with a 30 second pause between second application. Samples were allowed to dry 16-24 hours. Samples were soaked in artificial sebum for 1 hour at which time they were brushed on Canson Montval Watercolor Acuarela cards 10 times. The amount of product transfer was rated as compared to Reference Example 1. A ranking of 1 was better than the reference and a rating of 2 was equal to the reference and a rating of 3 was worse than the reference. The compositions were also compared with known market references known or claimed to contain high levels of oils (Competitor A and Competitor B).

Water Removal: Experiments were run in triplicate. 30 strokes of product were applied to fake eyelashes in 15 stroke sets, 30 second 16-24 hours. Samples were allowed to dry for 1 hour. Cotton pads were soaked with 1.5 mL of water. Fake lash was held between the cotton pad for 10 seconds, then withdrawn gently. The process was repeated until no additional product was removed. The number of pads used to remove the mascara completely was counted. The less the number of pads, the easier the mascara to remove with water.

Gloss: Gloss was measured using a BYK Gardner micro glossmeter and following the ASTM Standard Test Method for determining Gloss. Gloss measurements were determined on 3.0 mil drawdowns of formulas on Laneta Black and White draw down cards. "Drawdown" is a term of art in the cosmetic industry. In this procedure, the products were scooped and spread evenly on the cards using a metal "drawdown" bar. Once the films dried (24 hours after application), the shine of the resulting films was measured on a BYK Gardner micro glossmeter. The measurements were reported in gloss units (GU) which represent the ratio of reflected to incident light of the films compared to that for a standard. Low gloss is a GU value of less than 10 GU at an angle of 60°. The results are reported as an average of three trials.

Dynamic Mechanical Analysis: TA Instruments Q80 DMA were used. 3 miL wet drawdown (as used above) films were prepared on Teflon plates. Samples were allowed to dry in a hood for 72 hours. The method used included the following steps: 1. Equilibrate at 25° C.; 2. Isothermal for 2.00 min; 3. Ramp strain 5.000%/min to 200,000%; 4. End of method. Young's Modulus of the films was determined from the initial slope of the Stress (MPa) versus Strain (%) curve. The lower the Young's Modulus, the softer the film is.

Example VI

Testing Results

As described below, the inventive compositions were compared to Reference 1 as well as external competitor products which revealed that high levels of oils could be incorporated into the inventive compositions with little to no impact on the in vitro performance of the mascara. This was an unexpected result, as those skilled in the art would believe that the addition of high levels of oils would negatively impact wear of a mascara product.

Gloss: Gloss values (GU) of 3 miL drawdowns for inventive compositions versus Reference 1 and commercial products were determined. Results are reported as an average ±standard deviation.

| Example | % Oil | GU at 60° | GU at 85° |
|---|---|---|---|
| Reference | 0 | 5.4 ± 0.1 | 28.8 ± 1.3 |
| Competitor C | 0 | 7.5 ± 0.3 | 23.4 ± 0.6 |
| Competitor A | n.d. | 1.3 ± 0.1 | 3.8 ± 0.2 |
| Competitor B | n.d. | 0.5 ± 0.0 | 2.1 ± 0.1 |
| Example 1 | 5 | 4.4 ± 0.1 | 34.7 ± 0.9 |
| Example 2 | 5 | 5.0 ± 0.1 | 39.9 ± 0.8 |
| Example 3 | 5 | 4.8 ± 0.1 | 31.9 ± 0.7 |
| Example 4 | 2.5 | 4.5 ± 0.1 | 32.4 ± 0.5 |
| Example 5 | 2.5 | 8.8 ± 0.1 | 52.1 ± 0.3 |
| Example 6 | 2.5 | 6.4 ± 0.0 | 44.9 ± 1.1 |
| Example 7 | 1 | 3.4 ± 0.0 | 27.1 ± 0.4 |
| Example 8 | 1 | 4.6 ± 0.1 | 32.7 ± 0.0 |
| Example 9 | 1 | 3.6 ± 0.1 | 22.9 ± 0.7 |
| Example 10 | 3.5 | 4.9 ± 0.0 | 33.9 ± 1.0 |
| Example 11 | 5 | 5.7 ± 0.1 | 28.2 ± 0.5 |

For materials with less than 10 GU at 60°, an angle of 85° was used to obtain more accurate comparisons. The results clearly show that, unexpectedly, the addition of the more polar oil at increasing concentration does not appear to proportionally enhance shine (1-5%). Further, the addition of non-polar oil appears to add the highest achievable gloss at a peak oil concentration of 2.5%. Inventive compositions have a higher gloss at 85° than Competitor A and B, which also claim to have oils in their compositions. Finally, the combinations of oils do not result in increased levels of shine—the results are not additive. Rather, the peak was at about 30 GU at 85°.

Viscosity: Data compiled below demonstrates a trend with regard to the respective examples versus the Reference 1 without oils.

| Example | Apparent Viscosity (Pa · s) |
|---|---|
| Reference | 92-92.6 |
| Example 1 | 102.1-104.8 |
| Example 2 | 98.8-103.2 |
| Example 3 | 85.2-85.4 |
| Example 4 | 63.6 |
| Example 5 | 94.2-95.6 |
| Example 6 | 70.8-73.6 |
| Example 7 | 61.0-62.2 |
| Example 8 | 69.2-71.4 |
| Example 9 | 75.2-77.0 |
| Example 10 | 73.8-76.4 |
| Example 11 | 80.8-82.6 |

It was surprisingly discovered that the non-polar oils increased the apparent viscosity overall more than the polar oil, even at the same use level. The increase in viscosity can have an impact on the charge of the mascara on the lashes. Overall, the addition of the oils at increasing concentrations increased the apparent viscosity. Non-polar oil reached an apparent thickening plateau at 2.5%.

Texture Analysis: Data was compiled from experiments run according to procedure above at different times. Results are reported as an average ±standard deviation.

| Example | % Additive | Average Hardness ± stdevp (grams, g) |
|---|---|---|
| Reference | 6 | 26.18 ± 1.05 |
| Example 1 | 5 | 26.18 ± 0.55 |
| Example 2 | 5 | 29.44 ± 0.92 |
| Example 3 | 5 | 30.02 ± 0.58 |
| Example 4 | 2.5 | 29.92 ± 0.43 |
| Example 5 | 2.5 | 27.61 ± 1.33 |
| Example 6 | 2.5 | 18.17 ± 0.47 |
| Example 7 | 1 | 17.45 ± 0.50 |
| Example 8 | 1 | 25.14 ± 0.70 |
| Example 9 | 1 | 18.48 ± 0.53 |
| Example 10 | 5 | 21.05 ± 0.41 |
| Example 11 | 5 | 36.29 ± 0.14 |

Mascara formulas with increasing levels of oils showed increasing hardness, the values obtained being comparable to the Reference 1 formula with filler. The results show that oils can used to replace fillers in the Reference Example 1 formula.

Ease of removal: The lower number of pads used to remove mascara corresponded to easier removal properties. The average number of pads to remove mascara from fake lashes (n=3).

| Example | Fla# | Average # of pads to remove mascara |
|---|---|---|
| Reference | | 4 |
| Example 1 | | 3.3 |
| Example 2 | | 3.3 |
| Example 3 | | 3.7 |
| Example 4 | | 3.3 |
| Example 5 | | 2.3 |
| Example 6 | | 3.0 |
| Example 7 | | 3.3 |
| Example 8 | | 2.3 |
| Example 9 | | 3.0 |
| Example 10 | | 3.3 |
| Example 11 | | 3.3 |

In general, the addition of the oil increased the ease of removal in comparison to the Reference 1 formula, as fewer water soaked pads were needed to remove the mascaras. In addition, surprisingly, the non-polar oils tended to be easier to remove than formulas with polar oil.

Extreme flake: Flaking was visually rated on a scale from 1-4 (low flake to high flake). Rating of 1 was given for mascaras that visually flaked comparable to Competitor D, which has a high level of film former and is known to not flake a great deal. A rating of 4 was given to those that flake comparable to Competitor E, a formula without film former that is known to flake. Data was compiled from experiments run on different days (n=3).

| Example | Average Flake rating (n = 3) |
|---|---|
| Reference | 1-2 |
| Example 1 | 2 |
| Example 2 | 2 |
| Example 3 | 2 |
| Example 4 | 3 |
| Example 5 | 3 |

-continued

| Example | Average Flake rating (n = 3) |
|---|---|
| Example 6 | 3 |
| Example 7 | 3 |
| Example 8 | 4 |
| Example 9 | 3 |
| Example 10 | 2 |
| Example 11 | 1-2 |
| Competitor D | 1 |
| Competitor E | 4 |

Unexpectedly, formulas with lower concentration of oils (1%) tended to flake more, while those with a higher concentration of oils flaked less. The results obtained were independent of oil used.

Extreme smudging: A rating of 1-4 was given from visual examination. Formulas that smudged less than the Reference 1 Formula (without oils) were given a rating of 1, those that smudged equivalently to Reference 1 were rated 2, and those that smudged more were rated 3. Data was compiled from experiments run on different (n=3).

| Example | Smudge rating |
|---|---|
| Reference | 2 |
| Example 1 | 3 |
| Example 2 | 3 |
| Example 3 | 3 |
| Example 4 | 2 |
| Example 5 | 3 |
| Example 6 | 2 |
| Example 7 | 1 |
| Example 8 | 2 |
| Example 9 | 1 |
| Example 10 | 2 |
| Example 11 | 2 |
| Competitor A | 4 |
| Competitor B | 4 |
| Competitor E | 4 |
| Competitor D | 4 |

In contrast to Competitors A and B, which claim to have high oil content, the high levels of oils added into the inventive compositions did not significantly impact in vitro smudge. These results are unexpected as oils are thought to those skilled in the art to enhance smudging.

Dynamic Mechanical Analysis: Young's modulus of mascara films was determined as described above.

| Example | Average Film Width (mm) | Average Young's Modulus (E, MPa) ± Stdev |
|---|---|---|
| Reference | 0.061 | 42.3 ± 4.4 (n = 2) |
| Example 1 | 0.076 | 11.7 ± 1.6 (n = 3) |
| Example 2 | 0.088 | 10.8 ± 2.6 (n = 2) |
| Example 3 | 0.086 | 9.82 ± 5.2 (n = 3) |
| Example 4 | 0.063 | 20.2 ± 1.2 (n = 2) |
| Example 5 | 0.038 | 35.6 ± 3.2 (n = 2) |
| Example 6 | 0.0365 | 35.8 ± 2.2 (n = 2) |
| Example 7 | 0.0495 | 22.5 ± 2.8 (n = 2) |
| Example 8 | 0.058 | 16.1 ± 1.7 (n = 2) |
| Example 9 | 0.073 | 16.6 ± 7.6 (n = 3) |

The addition of the oils reduced the Young's Modulus, suggesting the addition of the oil enhanced the films' softness when compared to the Reference 1 formula (without oils). The most significant reduction in the brittleness of the film was observed for formulas containing 5% of oils. The result was unexpected as it was though that coherent films could not be obtained with this level of oils.

What is claimed is:

1. An composition comprising at least one dispersion of film forming particles in aqueous phase, at least one non-polar plant oil, and at least one polar plant oil,
    wherein the at least one polar plant oil is present in the composition in an amount ranging from about 0.5% to about 10% by weight with respect to the total weight of the composition,
    wherein the film forming particles and polar plant oil(s) are present in a film forming particles to polar plant oil weight ratio of from 10:1 to 1:1, and
    wherein (i) more polar plant oil is present in the composition by weight than non-polar plant oil or (ii) the same amount of polar plant oil and non-polar plant oil by weight are present in the composition.

2. The composition of claim 1, wherein the at least one polar plant oil is present in the composition in an amount of at least about 2% by weight with respect to the total weight of the composition.

3. The composition of claim 1, further comprising at least one coloring agent.

4. The composition of claim 1, further comprising at least one non-wax structuring agent.

5. The composition of claim 1, wherein the composition is a mascara.

6. The composition of claim 1, wherein the composition is wax-free.

7. The composition of claim 1, wherein the at least one non-polar plant oil is present in an amount ranging from about 0.2% to about 6% by weight based on the total weight of the composition.

8. The composition of claim 1, wherein the polar plant oil(s) and non-polar plant oil(s) are present in a polar plant oil to non-polar plant oil weight ratio of from 4:1 to 1:1.

9. The composition of claim 1, wherein the polar plant oil(s) and non-polar plant oil(s) are present in a polar plant oil to non-polar plant oil weight ratio of from 3:1 to 1:1.

10. The composition of claim 1, wherein the film forming particles and polar plant oil(s) are present in a film forming particles to polar plant oil weight ratio of from 8:1 to 1:1.

11. The composition of claim 1, wherein the film forming particles and polar plant oil(s) are present in a film forming particles to polar plant oil weight ratio of from 6:1 to 1:1.

12. The composition of claim 1, wherein the film forming particles and total plant oils are present in a film forming particles to plant oil weight ratio of from 20:1 to 1:5.

13. The composition of claim 1, wherein the film forming particles and total plant oils are present in a film forming particles to plant oil weight ratio of from 5:1 to 1:3.

14. The composition of claim 1, wherein the polar plant oil is castor oil.

15. The composition of claim 8, wherein the polar plant oil is castor oil.

16. The composition of claim 9, wherein the polar plant oil is castor oil.

17. The composition of claim 10, wherein the polar plant oil is castor oil.

18. The composition of claim 11, wherein the polar plant oil is castor oil.

19. The composition of claim 12, wherein the polar plant oil is castor oil.

20. A method of making up eyelashes comprising applying the composition of claim 1 to the eyelashes.

* * * * *